United States Patent
Kim et al.

(10) Patent No.: US 7,790,911 B2
(45) Date of Patent: Sep. 7, 2010

(54) ADVANCED PREPARATION METHOD OF ORGANIC-TRANSITION METAL HYDRIDE COMPLEXES AS HYDROGEN STORAGE MATERIALS

(75) Inventors: Jong Sik Kim, Daejeon (KR); Jeasung Park, Daejeon (KR); Hyo Jin Jeon, Incheon (KR); Hee Bock Yoon, Daejeon (KR); Dong Wook Kim, Daejeon (KR); Gui Ryong Ahn, Daejeon (KR); Dong Ok Kim, Seoul (KR); Jisoon Ihm, Seoul (KR); Moon-Hyun Cha, Seoul (KR)

(73) Assignee: Hanwha Chemical Corporation, Seoul (KR)

( * ) Notice: Subject to any disclaimer, the term of this patent is extended or adjusted under 35 U.S.C. 154(b) by 0 days.

(21) Appl. No.: 12/379,950

(22) Filed: Mar. 5, 2009

(65) Prior Publication Data

US 2009/0227808 A1    Sep. 10, 2009

(30) Foreign Application Priority Data

Mar. 5, 2008    (KR) .................. 10-2008-0020467

(51) Int. Cl.
*C07F 7/28* (2006.01)
*C01B 6/00* (2006.01)
*B01D 53/00* (2006.01)

(52) U.S. Cl. .................. 556/51; 423/645; 96/108
(58) Field of Classification Search .................. 556/51; 423/645; 96/108
See application file for complete search history.

(56) References Cited

U.S. PATENT DOCUMENTS 2,584,411 A  *  2/1952  Alexander .................. 75/395
3,376,107 A  *  4/1968  Oka .......................... 423/645

FOREIGN PATENT DOCUMENTS

| EP | 0 245 600 A2 | * 11/1987 |
| KR | 1020080024975 | 3/2008 |
| KR | 1020080024976 | 3/2008 |

* cited by examiner

*Primary Examiner*—Porfirio Nazario Gonzalez
(74) *Attorney, Agent, or Firm*—Clark & Brody

(57) ABSTRACT

The present invention relates to an advanced preparation method of organic-transition metal hydride used as hydrogen storage materials, the method including: preparing organic-transition metal-aluminum hydride complexes by reacting the organic-transition metal halide with metal aluminum hydride compounds; and preparing the organic-transition metal hydride by reacting the organic-transition metal aluminum hydride complexes with Lewis bases.

Since the preparation method of the organic-transition metal hydride according to the present invention does not use catalysts, it has advantages that it does not cause problems due to poisoning and can prepare the organic-transition metal hydride at high yield under less stringent conditions. The hydrogen storage materials containing the organic-transition metal hydride prepared from the preparation method can safely and reversibly store a large amount of hydrogen.

20 Claims, No Drawings

ADVANCED PREPARATION METHOD OF ORGANIC-TRANSITION METAL HYDRIDE COMPLEXES AS HYDROGEN STORAGE MATERIALS

TECHNICAL FIELD

The present invention relates to a preparation method of an organic-transition metal hydride as hydrogen storage materials that adsorbs and stores hydrogen and hydrogen storage materials containing the organic-transition metal hydride prepared therefrom.

BACKGROUND ART

An example of various hydrogen storage materials proposed by various study groups may include metallic hydrides, chemical hydrides (including $NaBH_4$, $KBH_4$, $LiBH_4$, and the like), metal-organic frameworks (MOF), nano structure materials (GNT, GNF, and the like), polymer-metal complex compounds, etc. However, the storage materials have problems in that: 1) hydrogen storage is less than a reference value (6wt. %) of minimum hydrogen storage proposed so as to practically use the hydrogen storage materials in Department of Energy (DOE) of USA, 2) the repeatability of the hydrogen storage is degraded, 3) hydrogen adsorption and desorption conditions are very stringent, 4) a material structure collapse phenomenon is caused in the hydrogen adsorption and desorption process, and 5) it is difficult to be commercialized due to a need to develop the reproduction process.

However, in the case of the organic-transition metal hydride complexes that are recently filed as patent by Hanwha Chemical R&D Center, it can be easily commercialized than the hydrogen storage materials according to the related art by Kubas binding of hydrogen and unique transition metals Ti, Sc, and V, since 1) a larger amount of hydrogen can be stored at higher efficiency, 2) hydrogen can be adsorbed and desorbed under less stringent conditions, e.g., the conditions that adsorption is performed under 25° C. and 30 atmospheric pressure and desorption is performed under 100° C. and 2 atmospheric pressure, and 3) there is little the structure collapse phenomenon at the time of performing the repetitive hydrogen adsorption and desorption (KR Patent Nos. 10-2007-0090753 and 10-2007-0090755).

The synthesis method of the organic-transition metal hydride disclosed in the above Patents proposes a method that includes hydrodehalogenation reaction (-M-X bond→-M-H bond) and simultaneously uses hydrogen feeding sources and catalysts as the hydrodehalogenation reaction. However, the hydrodehalogenation reaction, which simultaneously uses the hydrogen feeding sources and catalysts, has the following problems.

First, as problems associated with the poisoning phenomenon of the catalyst, $Cl^-$ ions produced during the reaction are adsorbed onto surfaces of catalysts to reduce active surface areas of catalysts and HCl produced during the reaction dissolves precious metal components of catalysts to reduce active sites of catalysts.

Second, as problems associated with a use of inorganic hydroxide necessary for the reaction, inorganic hydroxide used as neutralizers, which mitigate the poisoning phenomenon and the dissolution phenomenon, reacts with $Cl^-$ and HCl to produce the following reaction.

(for example) Case of using NaOH as inorganic hydroxide $NaOH+Cl^-\rightarrow NaCl+OH^-$ $NaOH+HCl\rightarrow NaCl+H_2O$ When organic solvents other than $H_2O$ are used, it is difficult to separate NaOH and target compounds from each other. Also, $OH^-$ approaches Ti—H bonding of the target compounds to form Ti—OH bonding and $H_2O$ approaches Ti—H bonding of a product and converts it into Ti oxide.

Third, as problems associated with separation and purification of products, since products are basically mixed with catalysts, it is difficult to separate them from each other. As a result, it is difficult to be applied to a commercialization process exceeding the scale obtained in the experiment.

Fourth, as problems associated with the used solvents, since 2-alkanols are used as the hydrogen feeding sources and the reaction solvents so as to increase the reaction efficiency, it is most preferable that a high boiling point is required to provide energy necessary for the complete hydrodehalogenation reaction to these 2-alkanols and the solvents including one or more α-H (α-hydrogen) as the hydrogen feeding sources are selected and applied. However, since the 2-alkanols having the above characteristics include an excessive hydrocarbon chain to produce various reaction by-products, there is a problem in that it is difficult to further separate and purify them.

Therefore, the typical hydrodehalogenation reaction using the hydrogen feeding sources and the catalysts has limitations in that it is difficult to stably prepare the organic-transition metal hydride complexes and the yield of products is low due to the above problems.

Disclosure

[Technical Problem]

Therefore, the present invention proposes to solve the above problems. It is an object of the present invention to provide a more stable reaction system and less stringent reaction conditions and a method capable of preparing targeted organic-transition metal hydride at higher efficiency.

Further, it is another object of the present invention to provide hydrogen storage materials containing organic-transition metal hydride prepared from the preparation method. Since the hydrogen storage material according to the present invention can store a large amount of hydrogen at high efficiency and adsorb and desorb hydrogen under relatively less stringent conditions than the hydrogen storage materials in the related art, they can be used as raw materials for driving a small and medium-sized fuel cell.

[Technical Solution]

The present invention provides a more stable reaction system and less stringent reaction conditions so as to solve the above proposed problems and is proposed to obtain organic-transition metal hydride, which is a target compound, at a higher yield. The present invention includes an advanced separation and purification method that does not use catalysts and inorganic hydroxide, which are components necessary for a typical hydrodehalogenation reaction system and performs washing without using distilled water.

In detail, a preparation method of organic-transition metal hydride according to the present invention includes:

1) preparing organic-transition metal-aluminum hydride complexes by reacting organic-transition metal halide with metal aluminum hydride (MAH) compounds; and 2) preparing the organic-transition metal hydride by reacting the organic-transition metal-aluminum hydride complexes with Lewis bases (LB).

In more detail, the present invention prepares the organic-transition metal hydride by using one or more of the metal aluminum hydrides (hereinafter, referred to as MAH) at step 1) (MAH method) as a reducing agent of the reaction step, inducing the complete dehalogenation reaction by controlling an amount of the reducing agent, forming desired organic-transition metal-aluminum hydride complexes, and prepares the organic-transition metal hydride by reacting the organic-transition metal-aluminum hydride complexes with amine compounds or carbanion compounds, which can act as Lewis bases (strong electron donor; hereinafter, referred to as LB).

The preparation method according to the present invention uses the organic-transition metal halide as a starting material to prepare the organic-transition metal hydride that is a target compound, wherein the organic-transition metal halide may be represented by the following Formula 2 and the organic-transition metal hydride may be represented by the following Formula 1.

  [Formula 1]

  [Formula 2]

In Formula 1 and Formula 2, A is an organic molecule and in detail, A is selected from an alkyl group of C2~C20, an aromatic ring of C6~C20, a fused ring having the aromatic ring, an aralkyl group where the alkyl group and the aromatic ring are mixed, A may be substituted by one or more substituent that is selected from halogen element, —$NO_2$, —NO, —$NH_2$, —$R^1$, —$OR^2$, —(CO)$R^3$, —$SO_2NH_2$, $SO_2X^1$, —$SO_2Na$, —$(CH_2)_kSH$, and —CN, wherein in the substituent, $R^1$ to $R^3$ are independently selected from a linear or branched alkyl group of C1~C30, or an aromatic group of C6~C20, $X^1$ is a halogen element, and k is an integer of 0 to 10.

To be concrete, in A, alkyl is selected from linear or branched aliphatic alkyl of C2~C20 or cycloaliphatic alkyl of C5~C7 and may include unsaturated bonding within a carbon chain and in A, carbon atoms forming the aromatic ring or the fused ring may be substituted with hetero atoms selected from nitrogen, oxygen, sulfur, or silicon (Si) and selected from the following structures.

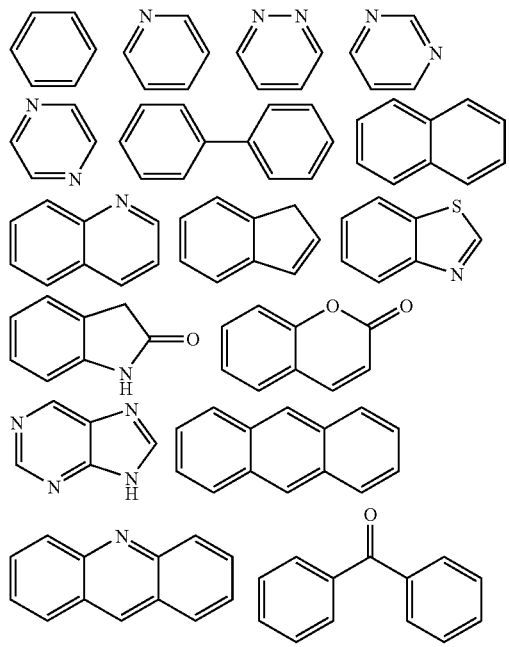

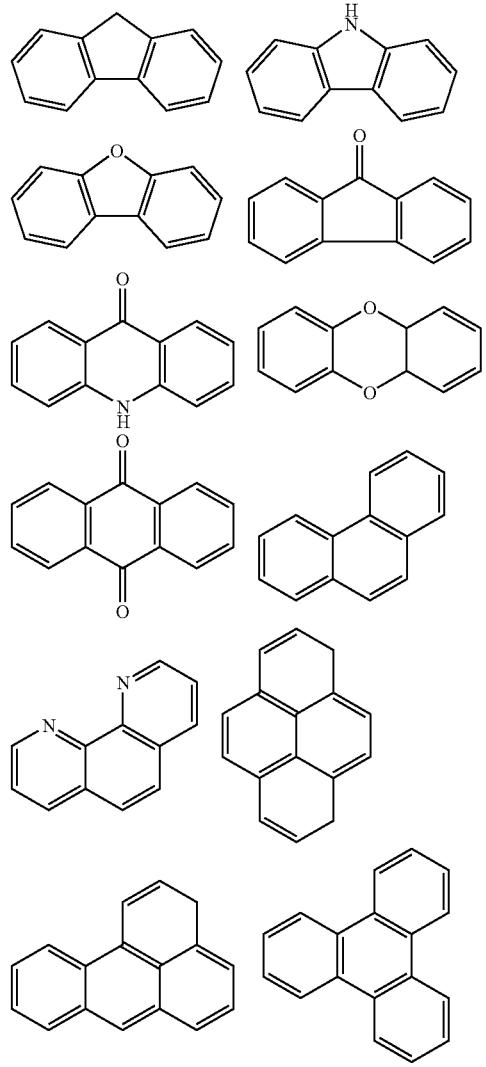

In Formula 1 and Formula 2, M is one or more that is selected from transition metal elements having valence of divalent or more, in detail, a valence range of M is 2 to 7, and in more detail, M is one or more selected from Ti, V, or Sc.

In Formula 1 and Formula 2, m is an integer where the valence of M minus 1 in detail an integer of 1 to 6, in more detail, an integer of 2 to 4.

In Formula 1 and Formula 2, n is an integer of 1 to 1000, in detail an integer of 1 to 10, in more detail, an integer of 2 to 6.

In Formula 2, X is a halogen element selected from F, Cl, Br, or I.

Hereinafter, the present invention will be described in more detail step-by-step.

In the present invention, it is preferred that the reaction of each step is performed based on Schlenk technology under a glove box and an air stream of one or more of argon, nitrogen, and helium due to instability of reactants and products.

Step 1): Preparing the Organic-Transition Metal-Aluminum Halide Complexes

Step 1) is a step that prepares the organic-transition metal-aluminum hydride complexes by reacting the organic-transition metal halide with the metal aluminum hydride (MAH) compounds. The organic-transition metal-aluminum hydride complexes prepared at step 1) are recognized as compounds that a bridged hydrogen bond is formed between transition metal and aluminum. The inventors can find that the organic-transition metal-aluminum hydride complexes having a different structure are formed according to a used amount of the metal aluminum hydride (MAH) and in the reaction with Lewis base that is a subsequent step, reaction by-products bonded to terminates of the transition metal may be produced according to the structure of the organic-transition metal-aluminum hydride complexes without completely separating the halogen element.

Therefore, the reaction of step 1) uses MAH as a reducing agent, but controls an equivalence ratio for the organic-transition metal halide to minimize the production of the reaction by-products and uses one or more selected from aromatic hydrocarbon compounds that do not include oxygen atoms as reaction solvents so as to overcome the instability of reactants and products.

The metal aluminum hydride compounds (MAH) used at step 1) reaction is selected from $LiAlH_4$ (lithium aluminum hydride), $NaAlH_4$ (sodium aluminum hydride), $Mg(AlH_4)_2$ (magnesium aluminum hydride), $Ca(AlH_4)_2$ (calcium aluminum hydride), and mixtures thereof and the metal aluminum hydride compounds are used as preferably 1 to 10 equivalences, more preferably 1 to 3 equivalences for halogen elements of the organic-transition metal halide. In other words, since the halogen elements contained in the organic-transition metal halide represented by Formula 2 is n×m mol per 1 mol of the organic-transition metal halide, it is preferable to use 1 to 10 equivalences for the halogen elements so as to substitute all the halogen elements. This has problems in that when the used amount of MAN is less than 1 equivalence, it is difficult to sufficiently perform the dehalogenation reaction and when the used amount of MAH exceeds 10 equivalences, it is difficult to perform the complete separation from by-products (MAH, XCl, LiCl, and Al) in the separation process of the organic-transition metal-aluminum hydride complexes after the reaction.

It is preferable that the reaction of step 1) uses one or more selected from the aromatic hydrocarbon compounds that do not include oxygen atoms as the reaction solvents in order to overcome the instability of reactants and products. As the reaction solvents, one or more selected from benzene, toluene, and xylene may be used, but preferably, benzene, toluene, xylene, or mixtures thereof, which can easily use the Schlenk method, are used.

At step 1) reaction, the content of the organic-transition metal halide within the reaction solvent is 0.00001 to 1 mol/L (M), preferably 0.0001 to 0.5 mol/L (M), more preferably 0.001 to 0.1 mol/L (M). This is because when the content within the reaction solvent is less than 0.00001 mol/L (M), it is difficult to preferably progress the hydrodehalogenation reaction and when the content exceeds 1 mol/L (M), it is difficult to perform the complete separation from by-products in the separation process of the organic-transition metal-aluminum hydride complexes, which are target compounds, after the reaction.

Step 1) is performed at the reaction temperature of −80 to 50° C., preferably −30 to 40° C., more preferably 0 to 40° C. This is because when the reaction temperature is less than -80° C., the incomplete state of the reaction may occur and when the reaction temperature exceeds 50° C., the decomposition of the organic-transition metal-aluminum hydride complexes, which are the target compounds, may occur.

Step 1) is performed for the reaction time of 1 to 72 hours, preferably 1 to 48 hours, more preferably 1 to 36 hours. This is because when the reaction time is less than 1 hour, the incomplete state of the reaction may occur and when the reaction time exceeds 72 hours, the decomposition of the organic-transition metal-aluminum hydride complexes may occur.

After step 1) reaction is performed, it is preferable to use the organic solvent having preferred polarity in order to selectively separate the organic-transition metal-aluminum hydride complexes at the time of performing the separation and purification of the organic-transition metal-aluminum hydride complexes. The organic solvents having the preferred polarity use preferably any one selected from methanol, ethanol, propanol, butanol, and mixtures thereof, more preferably propanol and a mixture including propanol. This is because when methanol and ethanol having high polarity in alcohol are used, alkoxylation reaction of the organic-transition metal-aluminum hydride complexes may occur and which the organic-transition metal-aluminum hydride complexes should be dissolved together with the reaction by-products, it is difficult to selectively purify the organic-transition metal-aluminum hydride complexes. Further, when butanol is used, since the freezing point is high, it is difficult to selectively purify the organic-transition metal-aluminum hydride complexes.

Step 2): Preparation of Organic-Transition Metal-Hydride

Step 2) is a step that prepares the organic-transition metal-hydride by reacting the organic-transition metal-aluminum hydride complexes with the Lewis bases (strong electron donor) LB.

It is recognized that the Lewis base LB used at step 2) supplies electrons to aluminum (Al center) of the organic-transition metal-aluminum hydride complexes to induce the decomposition of bridged hydrogen bond between the transition metal and aluminum the organic-transition metal-aluminum hydride complexes, thereby forming the organic-transition metal-hydride.

As the Lewis bases, one or more selected from amine compounds or carbanion compounds may be used.

The amine compounds may use primary, secondary, or tertiary amine selected from the following Formula 3.

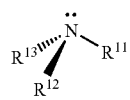

[Formula 3]

(In Formula 3, $R^{11}$ to $R^{13}$ are independently selected from hydrogen, a linear or branched alkyl group of C2 to C20, an aryl group of C6 to C20, and an aralkyl group where the alkyl group and the aryl group are mixed, wherein the carbon atoms of the alkyl, aryl, or aralkyl group may be substituted by hetero atoms selected from nitrogen, oxygen, sulfur, or silicon (Si) and the alkyl may include unsaturated bonding within a carbon chain. (However, $R^{11}$ to $R^{13}$ are not hydrogens at the same time).

It is preferable that the amine compound uses amine with an alkyl group having strong basicity as substituent, it is more preferably that $R^{11}$ to $R^{13}$ independently use amine having the number of carbon atoms, which are 6 or less, so as to increase solubility on the reaction solution, and it is most preferable that $R^{11}$ to $R^{13}$ use triethylamine that exists in a liquid phase at a normal temperature.

The carbanion compounds may use a lithium compound selected from the following Formula 4.

$R^{14}Li$ [Formula 4]

(In Formula 4, $R^{14}$ is selected from a linear or branched alkyl of C2 to C20, an aryl group of C6 to C20, and an aralkyl group where the alkyl group and the aryl group are mixed, wherein the alkyl may include unsaturated bonding within a carbon chain).

In more detail, it is preferable that the lithium compound uses alkyl lithium, which is a kind of $R^{14}$ and has a large number of carbon atoms included in $R^{14}$, so as to increase solubility on the reaction solution, it is more preferable that the lithium compound uses alkyl lithium having the number of carbon atoms, which are 6 or less, included in $R^{14}$ so as to prevent the kinds of the reaction by-products generated from diversifying, and it is most preferable that the lithium compound uses butyl lithium that exists in a liquid phase at a normal temperature.

It is preferable that the reaction of step 2) is performed under ethers solvents such as diethyl ether and tetrahydrofuran (THF) and it is more preferable that the reaction of step 2) uses tetrahydrofuran.

Further, when performing the separation purification process of the organic-transition metal hydride after the reaction of the step 2), it is preferable to use the organic solvents having preferred polarity in order to selectively separate the organic-transition metal hydride. As the organic solvents having preferred polarity, it is preferable to use any one selected from methanol, ethanol, propanol, butanol, and mixtures thereof. When 2-propanol is used, since the solubility of the reaction by-products is very largely degraded, it can easily separate and purify the organic-transition metal hydride and the reaction products, which are the target compounds. As a result, it is more preferable to use 2-propanol.

At step 2), the content of the organic-transition metal halide complexes is 0.00001 to 1 mol/L (M), preferably 0.0001 to 0.5 mol/L (M), more preferably 0.001 to 0.1 mol/L (M). This is because when the content within the reaction solvent is less than 0.00001 mol/L (M), the reaction rate is reduced and when the content exceeds 1M, it is difficult to perform the complete separation from by-products in the separation process of products after the reaction.

It is preferable that the Lewis base used at step 2) is used as 1 to 10 mol times, more preferably 1 to 3 mol times with respect to the organic-transition metal-aluminum hydride complexes.

Step 2) is performed at the reaction temperature of −80 to 50° C., preferably −30 to 40° C., more preferably 0 to 30° C. This is because when the reaction temperature is less than −80° C., the incomplete state of the reaction may occur and when the reaction temperature exceeds 50° C., the decomposition of the organic-transition metal-aluminum hydride complexes, which are the target compounds, may occur.

Step 2) is performed for the reaction time of 1 to 72 hours, preferably 1 to 48 hours, more preferably 1 to 24 hours. This is because when the reaction time is less than 1 hour, the incomplete state of the reaction may occur and when the reaction time exceeds 72 hours, the decomposition of the organic-transition metal-aluminum hydride complexes may occur.

Advantageous Effects

Since the preparation method according to the present invention overcomes the problems of separation and purification without using the expensive precious metal catalysts and inorganic hydroxide that are essential components of the hydrodehalogenation reation in the related art, the preparation method according to the present invention has advantages that it prepares the organic-transition metal hydride based on more stable reaction system, obtain the target compounds at a higher yield, and provide less stringent reaction conditions than the synthesis method according to the related art.

Further, since the organic-transition metal hydride prepared according to the present invention can store a large amount of hydrogen at high efficiency and adsorb and desorb hydrogen under relatively less stringent conditions, e.g., the conditions that adsorption is performed under 25° C. and 30 atmospheric pressure and desorption is performed under 100° C. and 2 atmospheric pressure, than the storage materials in the related art, it can be used as raw materials for driving a small and medium-sized fuel cell.

[Best Mode]

Experiments are performed based on the most detailed specifications on the two steps as described above. As organic-transition metal halide that is reactants, phenoxytitanium trichloride was selected since it is 1) is easily handled at normal temperature, 2) has a relatively large weight ratio of hydrogen storage due to organic-transition metal hydride having small molecular weight, which are target compounds, 3) does not agglomerate molecules due to an asymmetrical structure of each of the molecules to increase solubility on specific solvents and increase reaction efficiency.

A description of the experiments is provided to allow those skilled in the art to easily perform the present invention and therefore, the scope of the present invention is not limited thereto.

PREPARATION EXAMPLE 1

MAH Method I: Hydrodehalogenation Reaction 0.4 g (1.6 mmol) phenoxytitanium trichloride is dissolved (reactant II) with 30 ml toluene within a container of a 100 ml 2-neck round flask under argon air stream. 0.184 g (4.85 mmol) $LiAlH_4$ is dissolved (reactant I) with 70 ml toluene in a container of a 250 ml one-neck round flask under argon air stream. After a reflux is made at 25° C. for 36 hours while the reactant II slowly drops in the reactant I, the reaction is complete. Solvents are removed by a Schlenk method under argon atmosphere and then, only phenoxytitanium aluminum hydride complexes (target compounds A) are selectively extracted using 2-propanol from produced materials (as-synthesis material A). Thereafter, a 2-propanol is removed by the Schlenk method such that phenoxytitanium hydride (a target compound A) was obtained at a yield of 95%.

$^1$H-NMR ($CD_3CN$-$d_3$) δ (ppm): 7.28(d, 1H), 6.95(t, 2H), 6.85(t, 2H), 7.62(s, 1H), 4.83(s, 1H), 4.21 (s, 1H), −1.63(s, 1H), −2.23(s, 1H) ESI-MS (positive mode), m/z(relative intensity): [parent molecule]+ 171(9.9), 172(9.4), 173(100), 174(23), 175(10.1) Anal. Calc. for parent molecule: C, 41.6; H, 5.8. Found: C, 42.2; H, 5.2%.

In order to examine kinds of by-products prepared according to the preparing step and a preferred separation phenomenon of a target compound A having high selectivity, it can be appreciated from analysis results of XRD, $^{35}$Cl-NMR, and $^{27}$Al-NMR on the target compound A before the purification (As-synthesis) and the target compound A after the purification that LiCl and Al can be formed as main by-products through the preparing step. Further, it can be appreciated from analysis results of XRD and Ti (2p) XPS on the target compound A that LiCl and Al, which are by-products, and $LiAlH_4$, which are non-reactants, can be removed by the separation process using 2-propanol and the high-purity target compounds A can be obtained. The target compound A is recognized as the following structure.

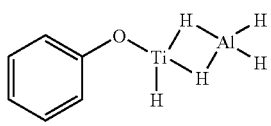

PREPARATION EXAMPLE 2

MAH Method II: Hydrodehalogenation Reaction

Phenoxytitanium aluminum hydride complexes (target compound A) were obtained at a yield of 96% by performing the same method except for using 0.262 g (4.85 mmol) $NaAlH_4$ instead of using $LiAlH_4$ in Example 1

$^1$H-NMR ($CD_3CN$-d3) δ (ppm): 7.28(d, 1H), 6.95(t, 2H), 6.85(t, 2H), 7.60 (s, 1H), 4.81 (s, 1H), 4.24(s, 1H), −1.61 (s, 1H), −2.29(s, 1H) ESI-MS (positive mode), m/z(relative intensity): [parent molecule]+ 171(9.9), 172(9.4), 173(100), 174(23), 175(10.1) Anal. Calc. for parent molecule: C, 41.6; H, 5.8. Found: C, 41.9; H, 5.5%.

In order to examine kinds of by-products prepared according to the MAH method II and the preferred separation phenomenon of the target compound A having high selectivity, it can be appreciated from analysis results of XRD, $^{35}$Cl-NMR, and $^{27}$Al-NMR on the target compound A before the purification (As-synthesis) and the target compound A after the purification that NaCl and Al can be formed as main by-products. Further, it can be appreciated from analysis results of XRD and Ti (2p) XPS on the target compound A that NaCl and Al, which are by-products, and $NaAlH_4$, which are non-reactants, can be removed by the separation process using 2-propanol and the high-purity target compounds A can be obtained.

Example 1

LB Method I: Hydrogenation Reaction 0.4 g (2.3 mmol) phenoxytitanium aluminum hydride complexes prepared according to Preparation Example 1 are dissolved (reactant IV) with 30 ml tetrahydrofuran (THF) within a container of a 100 ml 2-neck round flask under argon air stream. 0.70 g (6.9 mmol) trimethylamine is dissolved (reactant III) with 70 ml tetrahydrofuran (THF) in a container of a 250 ml one-neck round flask under argon air stream. After a reflux is made at 25° C. for 12 hours while the reactant IV slowly drops in the reactant III, the reaction is complete. Solvents are removed by a Schlenk method under argon atmosphere and then, only phenoxytitanium aluminum hydride complexes (target compounds B) are selectively extracted using 2-propanol from an as-synthesis material B. Thereafter, 2-propanol is removed by the Schlenk method such that phenoxytitanium hydride (a target compound B) was obtained at a yield of 98%.

$^1$H-NMR ($CD_3CN$-d3) δ (ppm): 7.28(d, 1H), 6.95(t, 2H), 6.85(t, 2H), 7.62 (s, 3H) ESI-MS (positive mode), m/z(relative intensity): [$C_6H_5$—O—Ti—$H_3$]+ 144(9.9), 145(9.4), 146(100), 147(23), 148(10.1) Anal. Calc. for $C_6H_5OTiH_3$: C, 50.0; H, 33.4. Found: C, 49.5; H, 33.7%.

In order to examine phenoxytitanium hydride (a target compound B) prepared according to the LB method I, XRD and XPS analysis was performed. It can be appreciated from the XRD analysis results that a unique structure of organic-inorganic complexes is formed and it can be appreciated from the XPS analysis results in Ti (2P) region of the target compound B that phenoxytitanium trihydride where predominant oxidizing number of Ti is +4 can be formed.

Example 2

LB Method II: Hydrogenation Reaction 0.4 g (2.3 mmol) phenoxytitanium aluminum hydride complexes prepared according to Preparation Example 1 are dissolved (reactant IV) with 30 ml tetrahydrofuran (THF) within a container of a 100 ml 2-neck round flask under argon air stream. 0.44 g (6.9 mmol) butyl lithium is dissolved (reactant III) with 70 ml tetrahydrofuran in a container of a 250 ml one-neck round flask under argon air stream. After a reflux is made at 25° C. for 16 hours while the reactant IV slowly drops in the reactant III, the reaction completes. Solvents are removed by a Schlenk method under argon atmosphere and then, only phenoxytitanium hydride (a target compound B) is selectively extracted using 2-propanol from an as-synthesis material 1. Thereafter, 2-propanol is removed by the Schlenk method such that phenoxytitanium hydride (target compounds B) were obtained at a yield of 95%.

$^1$H-NMR ($CD_3CN$-d3) δ (ppm): 7.28(d, 1H), 6.95(t, 2H), 6.85(t, 2H), 7.60 (s, 3H) ESI-MS (positive mode), m/z(relative intensity): [$C_6H_5$—O—Ti—$H_3$]+ 144(9.9), 145(9.4), 146(100), 147(23), 148(10.1) Anal. Calc. for $C_6H_5OTiH_3$: C, 50.0; H, 33.4. Found: C, 49.2; H, 34.0 %.

In order to examine phenoxytitanium hydride (target compounds B) prepared according to the LB method II, XRD and XPS analysis was performed. It can be appreciated from the XRD analysis results that unique structure of organic-inorganic complexes is formed and it can be appreciated from the XPS analysis results in a Ti (2P) region of the target compound B that phenoxytitanium trihydride where predominant oxidizing number of Ti is +4 can be formed.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A preparation method of organic-transition metal hydride, comprising:
   1) preparing organic-transition metal-aluminum hydride complexes by reacting organic-transition metal halide selected from the following formula 2 with metal aluminum hydride compounds; and
   2) preparing the organic-transition metal hydride selected from the following formula 1 by reacting the organic-transition metal-aluminum hydride complexes with Lewis bases A—(OMH$_m$)$_n$     [Formula 1]

A—(OMX$_m$)$_n$     [Formula 2]

[in Formula 1 or Formula 2, A is an organic molecule and M is a transition metal Ti; m is 3, n is 1, and X is a halogen element].

2. The preparation method of organic-transition metal hydride according to claim 1, wherein A of Formula 1 and Formula 2 is selected from an alkyl group of C2 to C20, an aromatic ring of C6 to C20, a fused ring having the aromatic ring, and an aralkyl group where the alkyl group and the aromatic ring are mixed.

3. The preparation method of organic-transition metal hydride according to claim 2, wherein in A of Formula 1 and Formula 2, alkyl is selected from a linear or branched aliphatic alkyl group of C2 to C20 or a cycloaliphatic alkyl group of C5 to C7 and includes unsaturated bonding within a carbon chain; in A, carbon atoms forming an aromatic ring or a fused ring are substituted with hetero atoms selected from nitrogen, oxygen, sulfur, or silicon (Si); A is substituted by one or more substituent that is selected from halogen elements, —$NO_2$, —NO, —$NH_2$, —$R^1$, —$OR^2$, —(CO)$R^3$, —$SO_2NH_2$, $SO_2X^1$, —$SO_2Na$, —$(CH_2)_kSH$, and —CN, wherein in the substituent, $R^1$ to $R^3$ are independently selected from a linear or branched alkyl group of C1 to C30, or an aromatic group of C6 to C20, $X^1$ is a halogen element, k is an integer of 0 to 10.

4. The preparation method of organic-transition metal hydride according to claim 3, wherein in A of Formula 1 and Formula 2, the aromatic ring or the fused ring is selected from the following structures

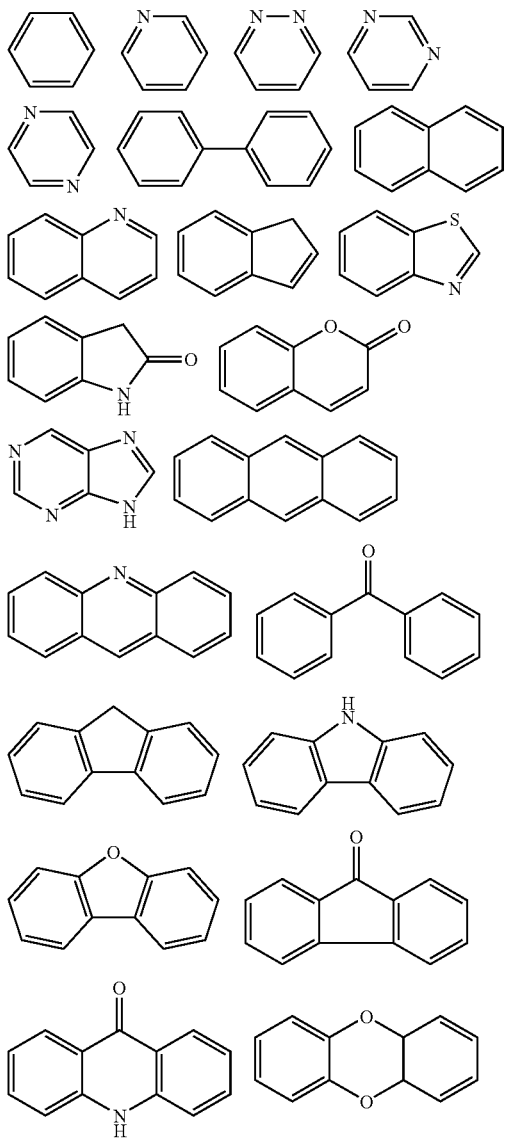

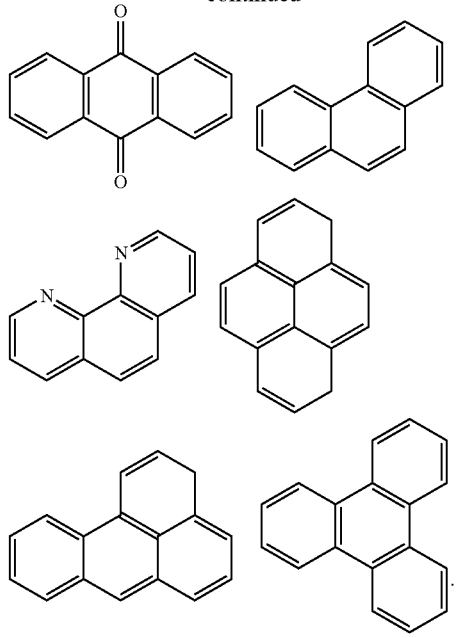

5. The preparation method of organic-transition metal hydride according to claim 1, wherein the metal aluminum hydride compounds are selected from lithium aluminum hydride ($LiAlH_4$), sodium aluminum hydride ($NaAlH_4$), magnesium aluminum hydride ($Mg(AlH_4)_2$), calcium aluminum hydride ($Ca(AlH_4)_2$), and mixtures thereof.

6. The preparation method of organic-transition metal hydride according to claim 1, wherein the Lewis base is selected from amine compounds or carbanion compounds.

7. The preparation method of organic-transition metal hydride according to claim 6, wherein the amine compound is selected from the following Formula 3

[Formula 3]

[In Formula 3, $R^{11}$ to $R^{13}$ are independently selected from hydrogen, a linear or branched alkyl group of C2 to C20, an aryl group of C6 to C20, and an aralkyl group where the alkyl group and the aryl group are mixed, wherein the carbon atoms of the alkyl, aryl, or aralkyl group are substituted by hetero atoms selected from nitrogen, oxygen, sulfur, or silicon (Si) and the alkyl includes unsaturated bonding within a carbon chain, however, $R^{11}$ to $R^{13}$ are excluded when they are hydrogen].

8. The preparation method of organic-transition metal hydride according to claim 6, wherein the carbanion compound is an alkyl lithium compound selected from the following Formula 4

$R^{14}Li$  [Formula 4]

(In Formula 4, $R^{14}$ is selected from a linear or branched alkyl group of C2 to C20, an aryl group of C6 to C20, and an aralkyl group where the alkyl group and the aryl group are mixed, wherein the alkyl includes unsaturated bonding within a carbon chain).

9. The preparation method of organic-transition metal hydride according to claim 1, wherein step 1) is made under one or more solvent selected from aromatic hydrocarbon compounds that do not include oxygen atoms.

10. The preparation method of organic-transition metal hydride according to claim 9, wherein after step 1), the organic-transition metal-aluminum hydride complexes are separated using polarity solvent selected from methanol, ethanol, propanol, butanol, and mixtures thereof.

11. The preparation method of organic-transition metal hydride according to claim 10, wherein at step 1), the content of the organic-transition metal halide is 0.00001 to 1 mol/L (M).

12. The preparation method of organic-transition metal hydride according to claim 11, wherein at step 1), the metal aluminum hydride compound is used at an equivalent amount of 1 to 10% by weight relative to the halogen elements of the organic-transition metal halide.

13. The preparation method of organic-transition metal hydride according to claim 9, wherein at step 1), reaction temperature is −80° C. to 50° C. and reaction time is 1 to 72 hours.

14. The preparation method of organic-transition metal hydride according to claim 1, wherein step 2) is made under one or more solvent selected from ethers.

15. The preparation method of organic-transition metal hydride according to claim 14, wherein the solvent is tetrahydrofuran (THF).

16. The preparation method of organic-transition metal hydride according to claim 14, wherein after step 2), the organic-transition metal hydride is separated using polarity solvent selected from methanol, ethanol, propanol, butanol, and mixtures thereof.

17. The preparation method of organic-transition metal hydride according to claim 15, wherein at step 2), the content of the organic-transition metal-aluminum hydride complex is 0.00001 to 1 mol/L (M).

18. The preparation method of organic-transition metal hydride according to claim 17, wherein at step 2), the Lewis base is used as 1 to 10 mol times with respect to the organic-transition metal-aluminum hydride complexes.

19. The preparation method of organic-transition metal$_{13}$ hydride according to claim 14, wherein at step 2), reaction temperature is −80° C. to 50° C. and reaction time is 1 to 72 hours.

20. A hydrogen storage material containing organic-transition metal hydride prepared from the preparation method according to claim 1.

* * * * *